United States Patent [19]

Donate et al.

[11] Patent Number: 4,956,017

[45] Date of Patent: Sep. 11, 1990

[54] NON-VOLATILE 1,1,1-TRICHLOROETHANE INHIBITORS

[75] Inventors: Felipe A. Donate; George E. Hartwell, both of Midland, Mich.; Bruce D. DeBolt, Surfside, Tex.; James G. Papajesk, Bay City, Mich.; Mark V. Buzzard, Chicago, Ill.

[73] Assignee: The Dow Chemical Company, Midland, Mich.

[21] Appl. No.: 348,246

[22] Filed: May 5, 1989

[51] Int. Cl.$^5$ ................................................ C08K 5/02
[52] U.S. Cl. ...................................... 106/311; 570/109; 570/110; 570/116; 570/117; 570/118
[58] Field of Search ................ 106/311; 570/118, 109, 570/110, 116, 117

[56] References Cited

U.S. PATENT DOCUMENTS

| | | | |
|---|---|---|---|
| 889,002 | 8/1971 | Blankenship et al. | 260/652.5 R |
| 2,964,572 | 12/1960 | Miller et al. | 570/118 |
| 3,002,028 | 9/1961 | Haefner et al. | 260/652.5 |
| 3,074,890 | 1/1963 | Grammer | 252/171 |
| 3,361,833 | 1/1968 | Blodgett | 570/118 |
| 3,873,631 | 3/1975 | Beckers et al. | 260/652.5 R |
| 3,926,831 | 12/1975 | Sonnengrüber | 252/171 |
| 3,933,517 | 1/1976 | Vivian | 106/311 |
| 3,933,518 | 1/1976 | Vivian | 106/311 |
| 4,056,403 | 11/1977 | Cramer et al. | 134/22 R |
| 4,065,323 | 12/1977 | Cormany | 134/10 |
| 4,189,397 | 2/1980 | Allen | 252/171 |
| 4,326,924 | 4/1982 | Cummings | 203/6 |

*Primary Examiner*—William R. Dixon, Jr.
*Assistant Examiner*—Helene Klemanski
*Attorney, Agent, or Firm*—Paula S. Ruhr

[57] ABSTRACT

A solvent, 1,1,1-trichloroethane, is stabilized against corrosion by the addition of a non-volatile polyether or complex polyether having an average molecular weight of from about 550 to about 8500. A painting formulation is prepared using the stabilized solvent.

13 Claims, No Drawings

NON-VOLATILE 1,1,1-TRICHLOROETHANE INHIBITORS

BACKGROUND OF THE INVENTION

The present invention relates to inhibited 1,1,1-trichloroethane compositions.

The use of 1,1,1-trichloroethane as a solvent with applications in dry cleaning, industrial cleaning and degreasing operations is well-known. It is also known to use 1,1,1-trichloroethane as a solvent in adhesive, coating and ink formulations. The tendency of 1,1,1-trichloroethane to degrade in the presence of metals, particularly aluminum, and moisture is also recognized. Thus, it has long been customary to add stabilizing amounts of inhibitors to 1,1,1-trichloroethane to stabilize it against metal-induced decomposition and to prevent corrosive attack upon the metal surfaces in contact with it.

Numerous examples exist of inhibitor compositions which have been taught to be useful in the inhibition of 1,1,1-trichloroethane. U.S. Pat. No. 3,113,154 teaches that 1,1,1-trichloroethane is stabilized by a mixture of dioxolane, an amine and a mono-olefin. U.S. Pat. No. 3,397,148 teaches that 1,1,1-trichloroethane is stabilized against metal corrosion with dioxolane and an epoxide. U.S. Pat. No. 4,018,837 teaches that a mixture of (1) a monoepoxide, a monochloroepoxide or mixture thereof and (2) a three-component mixture selected from dioxane, dioxolane, trioxane, tertiary butyl alcohol and a nitroalkane is useful to stabilize 1,1,1-trichloroethane. U.S. Pat. No. 4,115,461 teaches generally that 1,1,1-trichloroethane may be stabilized using a mixture comprising an epoxide, dioxolane, a nitroalkane and an alcohol. U.S. Pat. No. 4,189,397 teaches that 1,1,1-trichloroethane is stabilized with a low molecular weight polyalkylene glycol monoalkyl ether. U.S. Pat. No. 3,074,890 teaches that diethylene glycol dimethyl ether stabilizes 1,1,1-trichloroethane against decomposition when in contact with aluminum. U.S. Pat. No. 2,371,645 teaches that certain ethers inhibit the corrosion of chlorinated solvents used in various degreasing processes.

The known inhibited 1,1,1-trichloroethane formulations are not without problems. Generally, these formulations have been developed for use in vapor degreasing and cold metal cleaning operations. Thus, the formulations known may not be well adapted for use in coating and ink applications. Further, many of the accepted inhibitors have become unacceptable from an environmental and/or toxicological perspective. Thus, what is lacking and what is needed is an inhibited 1,1,1-trichloroethane composition well adapted for use in coatings and inks which is environmentally acceptable.

SUMMARY OF THE INVENTION

In one aspect, the present invention is such a composition comprising 1,1,1-trichloroethane containing a stabilizing amount of a non-volatile polyether having at least one terminal moiety selected from the group consisting of hydroxy, amine, substituted amine, cyano, ether, ester and urethane.

In a second aspect, the present invention is a solvent-based paint formulation comprising from about 10 to about 90 volume percent 1,1,1-trichloroethane containing a stabilizing amount of a non-volatile polyether having at least one terminal moiety selected from the group consisting of hydroxy, amine, substituted amine, cyano, ether, ester and urethane.

It is surprising that the inhibited 1,1,1-trichloroethane composition of this invention is stable to metal corrosion, particularly to aluminum corrosion, results in high quality coating formulations and does not contain inhibitor components that are environmentally or toxicologically objectionable.

DETAILED DESCRIPTION OF ILLUSTRATIVE EMBODIMENTS

Polyethers useful in the practice of this invention have an average molecular weight of at least about 550 and no greater than about 8500. The polyethers are also non-volatile organic compounds or non-VOC compounds. By this it is meant that the polyethers have a volatile content of less than about 0.5 percent as determined by American Standard Test Method D-2369-81. The volatile content is preferably less than about 0.4 percent.

It is preferred that the polyethers useful in the practice of this invention correspond to the formula

$$A\text{\textlbrackdbl}(OCH_2CR^1H)_n X\text{\textrbrackdbl}_o \qquad (I)$$

wherein A is nitrogen or a $C_{1-10}$ monovalent or polyvalent organic radical: $R^1$ is hydrogen, methyl or ethyl: o is equal to the valency of A: n is at least about 4 and no greater than about 70, with the proviso that the average molecular weight is at least about 550 and no greater than about 8500: and X is a hydroxy, primary or secondary amine, ester, aliphatic ether, aromatic ether, urethane, cyano, alkoxy, epoxy or carboxy moiety.

In one preferred embodiment, the polyethers of this invention correspond to Formula I wherein A is a monovalent $C_{1-6}$ alkyl or a $C_{2-6}$ alkenyl: $R^1$ is hydrogen, methyl or ethyl with the proviso that $R^1$ can vary from one repeating unit to another: X is hydroxy or acetoxy. It is more preferred that A is methyl, allyl or butyl and n is a number such that the average molecular weight of the compound is at least about 1500 and no greater than about 2000.

In a second preferred embodiment, A is a derivative of a hexahydric alcohol substituted with a fatty acid ester and o is 1 or 2, preferably 2. Such compounds are available commercially from Imperial Chemical Industries under the trademark TWEEN.

In a third preferred embodiment of this invention, A is a $C_{2-10}$ organic radical having a valency of at least two. A is preferably derived from $C_{2-10}$ organic compounds having from two to ten active hydrogens. By active hydrogen is meant a hydrogen atom which, because of its position in the molecule, has significant activity by the Zerewitinoff test. Representative active hydrogens are those in the —COOH, —OH, —NH$_2$, CONH$_2$, —SH or —CONH— groups. In a preferred embodiment, the active hydrogen is present in an —OH group. Such compounds include, as non-limiting examples, glycerine, ethylene glycol, propylene glycol, cyclohexanediol, 1,2-dihydroxydecane, 1,2-butanediol, 1,4,7-trihydroxyoctane, sorbitol and mannitol. At least about two of the active hydrogen-containing groups present on A react to form polyether chains. $R^1$ is hydrogen, methyl or ethyl with the proviso that $R^1$ can vary from one repeating unit to another. The value of n is preferably at least about 4 and no greater than about 50 and more preferably at least about 20 and no greater than about 25.

In all preferred embodiments of Formula I, the polyether chain represented by

—(OCH$_2$CHR$^1$)$_n$— is an ethylene oxide polymer, a propylene oxide polymer, an ethylene oxide/propylene oxide copolymer, an ethylene oxide/butylene oxide copolymer or an ethylene oxide/propylene oxide/butylene oxide copolymer. When the polyether is an ethylene oxide/butylene oxide copolymer, it preferably contains at least about 50 mole percent ethylene oxide.

The compounds useful as inhibitors in this invention are available commercially or may be prepared by methods well-known to those skilled in the art. For example, simple polyethers may be prepared by the condensation of ethylene oxide, propylene oxide and/or butylene oxide initiated by water or an alcohol. Amine terminated polyethers may be prepared by aminating the polyethers and then adding an aldehyde or ketone to form the imine and then reducing it to form the secondary amine.

The polyethers represented by Formula I where A is a derivative of a hexahydric alcohol may be prepared by methods known in the art as discussed, for example, in U.S. Pat. No. 4,297,290. The polyethers are prepared by forming anhydro sorbitol by acid-catalyzed anhydrization and then reacting the resulting anhydro sorbitol with a fatty acid in the presence of a base. This product is then ethoxylated by known methods.

The complex polyethers represented by Formula I where A is a C$_{2-10}$ polyvalent radical are available commercially or may be prepared by methods well-known to those skilled in the art. For example, such complex polyethers are available from The Dow Chemical Company under the trademark VORANOL and from Texaco under the trademark JEFFAMINE. Such compounds may be prepared by condensation of ethylene oxide, propylene oxide and/or butylene oxide with a starting compound such as glycerine and then catalytically aminating the polyether as taught in U.S. Pat. No. 4,153,581 hereby incorporated by reference.

Examples of polyethers useful in the practice of this invention include ethylene oxide/propylene oxide copolymer (50/50 mole percent) with terminal allyl and hydroxy groups with an average molecular weight of about 1800, ethylene oxide polymer with terminal allyl and acetoxy groups with an average molecular weight of about 550, ethylene oxide/propylene oxide copolymer (50/50 mole percent) with terminal allyl and acetoxy groups with an average molecular weight of about 1800, ethylene oxide polymer with terminal methoxy and hydroxy groups with an average molecular weight of about 750, ethylene oxide polymer with an average molecular weight of about 600, propylene oxide polymer with an average molecular weight of about 4000, propylene oxide polymer with an average molecular weight of about 2000, propylene oxide polymer with an average molecular weight of about 1200, ethylene oxide/butylene oxide copolymer (50/50 mole percent) with an average molecular weight of about 800, polypropylene oxide triol with an average molecular weight of about 3000, amine capped polypropylene oxide triol with a molecular weight of about 3000, isopropylamine capped polypropylene oxide triol with an average molecular weight of about 3000, TWEEN ® 20 complex ester-ether, TWEEN ® 60 complex ester-ether, and TWEEN ® 80 complex ester-ether.

Preferred polyethers useful in the practice of this invention include a hydroxy and allyl terminated copolymer of 50 mole percent ethylene oxide and 50 mole percent propylene oxide with an average molecular weight of about 1800 and a hydroxy terminated propylene oxide polymer with a molecular weight of about 1200.

The amount of polyether used to stabilize 1,1,1-trichloroethane is any which has a stabilizing effect. It is preferred to use at least about 0.05 weight percent and no greater than about 10.0 weight percent based on the total amount of solvent and inhibitor. It is more preferred to use at least about 2.0 and no greater than about 4.0 weight percent.

In addition to the polyether, the inhibited 1,1,1-trichloroethane composition of this invention may contain additional additives such as acid acceptors and metal passivators known in the art.

Acid acceptors useful in the practice of this invention include epoxidized natural oils such as epoxidized linseed oil or epoxidized soybean oil, preferably epoxidized linseed oil. Other useful acid acceptors include butylene oxide, isoamylene epoxide and substituted and unsubstituted C$_{3-6}$ monoepoxides such as epichlorohydrin.

Metal passivators useful in the composition of this invention include nitroalkanes such as nitromethane, nitroethane and 1-nitropropane. Other metal passivators known in the art may also advantageously be used. It is preferred to use nitromethane as a metal passivator.

A particularly preferred embodiment of the invention is the composition consisting essentially of about 97.3 weight percent 1,1,1-trichloroethane, about 2.5 weight percent of a 50/50 mole percent ethylene oxide/propylene oxide copolymer with an average molecular weight of about 1700 to 2300 and with terminal allyl and hydroxy groups, about 0.05 weight percent butylene oxide and about 0.1 weight percent nitromethane.

The composition of the present invention is useful in formulation of low VOC coatings and inks. In a preferred embodiment, the invention comprises a solvent-based paint formulation comprising from about 10 to about 90 volume percent 1,1,1-trichloroethane containing a stabilizing amount of a non-volatile polyether having at least one terminal moiety selected from the group consisting of hydroxy, amine, substituted amine, cyano, ether, ester and urethane. It is preferred that the paint formulation comprise from about 40 to about 60 volume percent of the stabilized 1,1,1-trichloroethane. The following examples are provided to illustrate the invention and should not be interpreted as limiting it in any way. Unless stated otherwise, all parts and percentages are by weight.

EXAMPLE 1 ALUMINUM SCRATCH TEST

A 20-ml portion of 1,1,1-trichloroethane containing the percentage of the inhibitor identified in Table I below is placed in a 2-ounce Kerr jar containing a 1-inch by 1-inch by 1/16-inch coupon of 1100 aluminum. The coupon is scratched in a 3-line by 3-line cross hatch pattern using a steel septum tool. The coupon is observed at timed intervals: initial, 5 minutes, 10 minutes, 15 minutes, 30 minutes and 1 hour. A numerical evaluation is given to each test one hour after scratching. The following ratings are used:

0 = complete inhibition
1 = slight formation of reaction products on scratches
2 = medium formation of reaction products on scratches 3=medium formation of reaction products on scratches: solution has slight yellow color
4=heavy formation of reaction products on scratches: solution has yellow, amber or brown color
5=runaway reaction within one hour The results obtained are shown in Table I below.

TABLE I

| Inhibitor① | Concentration (Wt. %) | Rating |
|---|---|---|
| None | — | 5.00② |
| EO/PO copolymer with terminal allyl and hydroxy groups; MW 1800 | 4.00 | 1.00 |
| EO homopolymer with terminal allyl and acetoxy groups; MW 550 | 4.00 | 1.00 |
| EO/PO copolymer with terminal allyl and acetoxy groups; MW 1800 | 4.00 | 0.00 |
| EO homopolymer with terminal methoxy and hydroxy groups; MW 750 | 4.00 | 1.50 |
| EO homopolymer; MW 600 | 4.00 | 1.00 |
| PO homopolymer; MW 4000 | 4.00 | 1.00 |
| PO homopolymer; MW 2000 | 4.00 | 1.00 |
| PO homopolymer; MW 1200 | 4.00 | 0.00 |
| EO/BO copolymer; MW 800 | 3.00 | 1.00 |
| Tween ® 20③ | 4.00 | 0.00 |
| Tween ® 60③ | 4.00 | 1.00 |
| Tween ® 80③ | 4.00 | 0.00 |
| Polypropylene oxide triol; MW 3000 | 3.00 | 0.00 |
| Polypropylene oxide triol; amine capped; MW 3000 | 3.00 | 0.00 |
| Polypropylene oxide triol capped with isopropylamine; MW 3000 | 3.00 | 0.00 |

①EO = ethylene oxide; PO = propylene oxide; BO = butylene oxide.
②Not an example of the invention; vigorous reaction within 10 minutes.
③Tween is a registered trademark of Imperial Chemical Industries for a nonionic surface-active ester-ether.

The data in the above table indicates that the polyethers of the present invention are generally effective a aluminum corrosion inhibitors.

EXAMPLE 2 BLENDER TESTS

A 100-ml portion of 1,1,1-trichloroethane containing the inhibitor at a concentration of 3.0 weight percent as specified in Table II is placed in a Waring blender. Aliquots of the solution are analyzed by titration and gas chromatography to determine the weight percent of vinylidene chloride (VDC) and 1,1-dichloroethane and the milliequivalents per milliliter of chloride ion and hydrogen ion. This is reported in Table II below in the "Before" row. Next, 10.0 grams of 2024 aluminum shavings are added and then a glass plate is sealed on top of the blender using a high vacuum silicone grease. The blender is then started and operated at 15,500 revolutions per minute (rpm) for ten minutes or until the solution turns black and foams excessively. The blender is stopped after ten minutes and aliquots of the product solution are analyzed by titration and gas chromatography to determine the weight percent of vinylidene chloride (VDC) and 1,1-dichloroethane and the milliequivalents per milliliter of chloride ion and hydrogen ion. This is reported in Table II below in the "After" row. The data obtained using various inhibitors is presented in Table II below.

TABLE II

| Inhibitor① | | VDC (Wt. %) | 1—1 Di (Wt. %) | Cl⁻ (meq/ml) | H⁺ (meq/ml) |
|---|---|---|---|---|---|
| EO/PO copolymer with terminal allyl and hydroxy groups; MW 1800 | Before | 0.019 | 0.004 | <0.00005 | 0.00030 |
| | After | 0.035 | 0.007 | 0.00806 | 0.02200 |
| EO homopolymer with terminal allyl and acetoxy groups; MW 550 | Before | 0.019 | 0.003 | <0.00005 | 0.00020 |
| | After | 0.032 | 0.006 | 0.00463 | 0.01619 |
| EO/PO copolymer with terminal allyl and acetoxy groups; MW 1800 | Before | 0.023 | 0.004 | <0.00005 | 0.00005 |
| | After | 0.093 | 0.009 | 0.01081 | 0.02100 |
| EO homopolymer with terminal allyl and hydroxy groups; MW 550 | Before | 0.018 | 0.003 | <0.00005 | 0.00030 |
| | After | 0.063 | 0.014 | 0.03261 | 0.06600 |
| PO homopolymer; MW 1200 | Before | 0.024 | 0.004 | <0.00005 | 0.00030 |
| | After | 0.257 | 0.029 | 0.02180 | 0.00200 |
| EO/BO copolymer; MW 800 | Before | 0.019 | 0.000 | <0.00005 | 0.00200 |
| | After | 0.034 | 0.009 | 0.02090 | 0.0500 |
| Tween ® 20② | Before | 0.018 | 0.000 | <0.00005 | 0.00005 |
| | After | 0.023 | 0.000 | 0.00923 | 0.00899 |
| Tween ® 60② | Before | 0.018 | 0.000 | <0.00005 | 0.00015 |
| | After | 0.059 | 0.017 | 0.03289 | 0.08500 |
| Tween ® 80② | Before | 0.018 | 0.000 | <0.00005 | 0.00005 |
| | After | 0.030 | 0.000 | 0.02504 | 0.03500 |
| Polypropylene oxide triol; MW 3000 | Before | 0.024 | 0.005 | <0.00005 | 0.00005 |
| | After | 0.044 | 0.036 | 0.05300 | 0.03000 |
| Polypropylene oxide triol capped with —NH₂; MW 3000 | Before | 0.026 | 0.003 | <0.00005 | 0.00005 |
| | After | 0.025 | 0.005 | 0.02264 | 0.00771 |
| Polypropylene oxide triol capped with isopropylamine; MW 3000 | Before | 0.027 | 0.003 | <0.00005 | 0.00030 |
| | After | 0.024 | 0.004 | 0.02450 | 0.01120 |

①EO = ethylene oxide; PO = propylene oxide; BO = butylene oxide.
②Tween is a registered trademark of Imperial Chemical Industries for a nonionic surface-active ester-ether.

The data presented in Table II demonstrates the effectiveness of the inhibitor compounds of the present invention in the more stringent blender tests. In each instance, a comparison of the sample analysis before the blender test and after the test indicates only nominal increases in the amounts of breakdown products after the contact with aluminum shavings thus indicating the effectiveness of this invention in stabilizing 1,1,1-trichloroethane from aluminum corrosion. Generally, amounts greater than about 1 percent for VDC, greater than about 0.3 percent for 1,1-di, greater than about 0.2 milliequivalents per milliliter for each of Cl— and H+ would indicate failure of the inhibitor.

EXAMPLE 3

A coating formulation is prepared using a stabilized solvent of this invention and commercially available paints. The paints used are a commercially available iron oxide alkyd primer and acrylic enamel topcoat. Two formulations are prepared. One uses CHLOROTHENE ™ SM brand solvent which is an inhibited 1,1,1-trichloroethane solvent commercially available from The Dow Chemical Company. The second formulation uses 1,1,1-trichloroethane inhibited with 3 percent of an ethylene oxide/propylene oxide copolymer with terminal allyl and acetoxy groups and an average molecular weight of about 1800. The formulations are prepared by diluting a commercial formulation with the inhibited solvent in a 1:1 volume ratio. The formulations are then tested for various properties and the results obtained are shown in Table III below.

TABLE III

| | CHLOROTHENE ™ SM Solvent | Test Solvent |
|---|---|---|
| Thickness (mils) (Test Method D1186) | | |
| Primer | 3.312 | 3.854 |
| Top Coat | 1.389 | 1.405 |
| Gloss (Test Method D523-80) | | |
| 60° | 89.7 | 93.7 |
| 20° | 82.4 | 90.5 |
| Cross Hatch Adhesion (Test Method D3359) | 97 | 89 |
| Pencil Hardness (Test Method D3363) | <5B | <5B |
| Mandrel Bend (G10-77) | Failed | Passed |
| Orange Peel (Visual Inspection) | Yes | No |

As is demonstrated by the above information, coating formulations prepared using the inhibited solvents of the present invention result in coatings with comparable or improved properties.

WHAT IS CLAIMED IS:

1. A composition comprising 1,1,1-trichloroethane containing a stabilizing amount of a non-volatile polyether with an average molecular weight of at least about 550 and no greater than about 8500 and having at least one terminal moiety selected from the group consisting of hydroxy, amine, substituted amine, cyano, ether, ester and urethane.

2. The composition of claim 1 wherein the polyether corresponds to the formula $$A\text{--}[(OCH_2CR^1H)_nX]_o \quad (I)$$

wherein A is nitrogen or a $C_1$-10 monovalent or polyvalent organic radical: $R^1$ is hydrogen, methyl or ethyl; o is equal to the valency of A; n is at least about 4 and no greater than about 70, with the proviso that the average molecular weight is at least about 550 and no greater than about 8500: and X is a hydroxy, primary or secondary amine, ester, aliphatic ether, aromatic ether, urethane, cyano, alkoxy, epoxy or carboxy moiety.

3. The composition of claim 2 wherein A is a monovalent $C_1$-6 alkyl or a $C_2$-6 alkenyl $R^1$ is hydrogen, methyl or ethyl with the proviso that $R^1$ can vary from one repeating unit to another; X is hydroxy or acetoxy.

4. The composition of claim 3 wherein A is methyl, allyl or butyl and n is a number such that the average molecular weight of the compound is at least about 1500 and no greater than about 2500.

5. The composition of claim 2 wherein A is a $C_2$-10 organic radical having from two to ten active hydrogen-containing substituents.

6. The composition of claim 5 wherein A is a $C_2$-10 organic radical having from two to ten hydroxy-containing substituents.

7. The composition of claim 6 wherein A is derived from glycerine, ethylene glycol, propylene glycol, cyclohexanediol, 1,2-dihydroxydecane, 1,2-butanediol, 1,4,7-trihydroxyoctane, sorbitol and mannitol.

8. The composition of claim 5 wherein n is at least about 4 and no greater than about 50.

9. The composition of claim 8 wherein n is at least about 20 and no greater than about 25.

10. A composition comprising 1,1,1-trichloroethane containing a stabilizing amount of a non-volatile polyether which corresponds to the formula

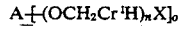

wherein A is a derivative of a hexahydric alcohol substituted with a fatty acid ester ; $R^1$ is hydrogen, methyl or ethyl and o is 1 or 2; n is at least about 4 and no greater than about 70, with the proviso that the average molecular weight is at least about 550 and no greater than about 8500; and X is a hydroxy, primary or secondary amine, ester, aliphatic ether, aromatic ether, urethane, cyano, alkoxy, epoxy or carboxy moiety.

11. The composition of claim 10 wherein o is 2.

12. A solvent-based paint formulation comprising paint and from about 10 to about 90 volume percent 1,1,1-trichloroethane containing a stabilizing amount of a non-volatile polyether with an average molecular weight of at least about 550 and no greater than about 8500 and having at least one terminal moiety selected from the group consisting of hydroxy, amine, substituted amine, cyano, ether, ester and urethane.

13. The formulation of claim 12 wherein the stabilized 1,1,1-trichloroethane comprises from about 40 to about 60 percent of the formulation.

* * * * *

UNITED STATES PATENT AND TRADEMARK OFFICE
CERTIFICATE OF CORRECTION

PATENT NO. : 4,956,017

DATED : September 11, 1990

INVENTOR(S) : Felipe A. Donate et al.

It is certified that error appears in the above-identified patent and that said Letters Patent is hereby corrected as shown below:

Column 2, line 26 "radical: R1" should correctly read --radical; $R^1$--.

Column 2, line 26 "ethyl:" should correctly read --ethyl;--.

Column 2, line 27 "A:" should correctly read --A;--.

Column 2, line 30 "8500:" should correctly read --8500;--.

Column 2, line 35 "alkenyl:" should correctly read --alkenyl;--.

Column 2, line 37 "another:" should correctly read --another;--.

Column 4, line 23 "$C_3$-6" should correctly read --$C_{3-6}$--.

Column 4, line 49, the sentence beginning with "The following examples are provided" should be indented to begin a new paragraph.

Column 5, line 2 "scratches:" should correctly read --scratches;--.

Column 5, line 3 "scratches:" should correctly read --scratches;--.

Column 5, line 61 "a" should correctly read --as--.

Column 7, line 44 "$A[-(OCH_2CR^1H)_nX]_o$" should correctly read --$A[-(OCH_2CR^1H)_nX]_o$--.

Column 7, line 46 "radical:" should correctly read --radical;--.

Column 7, line 51 "8500:" should correctly read --8500;--.

UNITED STATES PATENT AND TRADEMARK OFFICE
CERTIFICATE OF CORRECTION

PATENT NO. : 4,956,017

DATED : September 11, 1990

INVENTOR(S) : Felipe A. Donate et al.

It is certified that error appears in the above-identified patent and that said Letters Patent is hereby corrected as shown below:

Column 8, line 11 "$C_2$-10" should correctly read --$C_{2-10}$--.

Column 8, line 14 "$C_2$-10" should correctly read --$C_{2-10}$--.

Column 8, line 29 "$A[-(OCH_2Cr^1H)_nX]_o$" should correctly read --$A[-(OCH_2CR^1H)_nX]_o$--.

Signed and Sealed this

Fifth Day of May, 1992

Attest:

DOUGLAS B. COMER

*Attesting Officer*   Acting Commissioner of Patents and Trademarks